US010605641B2

(12) United States Patent
Badarlis et al.

(10) Patent No.: US 10,605,641 B2
(45) Date of Patent: Mar. 31, 2020

(54) MEASURING DEVICE AND METHOD FOR DETERMINING A CORRECTED MASS FLOW AND USES OF THE MEASURING DEVICE

(71) Applicant: Endress + Hauser Flowtec AG, Reinach (CH)

(72) Inventors: Anastasios Badarlis, Birsfelden (CH); Axel Pfau, Aesch (CH); Oliver Popp, Oberwil (CH); Vivek Kumar, Allschwil (CH); Hanno Schultheis, Lorrach (DE)

(73) Assignee: ENDRESS + HAUSER FLOWTEC AG, Reinach (CH)

( * ) Notice: Subject to any disclaimer, the term of this patent is extended or adjusted under 35 U.S.C. 154(b) by 289 days.

(21) Appl. No.: 15/037,125

(22) PCT Filed: Oct. 27, 2014

(86) PCT No.: PCT/EP2014/072972
§ 371 (c)(1),
(2) Date: May 17, 2016

(87) PCT Pub. No.: WO2015/074833
PCT Pub. Date: May 28, 2015

(65) Prior Publication Data
US 2016/0290849 A1    Oct. 6, 2016

(30) Foreign Application Priority Data

Nov. 19, 2013  (DE) .................. 10 2013 112 729
May 13, 2014   (DE) .................. 10 2014 106 729

(51) Int. Cl.
*G01F 15/02*    (2006.01)
*G01F 1/688*    (2006.01)
(Continued)

(52) U.S. Cl.
CPC .............. *G01F 15/02* (2013.01); *G01F 1/684* (2013.01); *G01F 1/688* (2013.01); *G01F 1/6845* (2013.01); *G01N 9/002* (2013.01); *G01N 11/16* (2013.01)

(58) Field of Classification Search
CPC ..................... G01F 1/684; G01F 1/6845
See application file for complete search history.

(56) References Cited

U.S. PATENT DOCUMENTS 5,235,844 A     8/1993   Bonne et al.
5,311,447 A  *  5/1994   Bonne ................. G01N 33/225
                                                        374/44
(Continued)

FOREIGN PATENT DOCUMENTS

CN       1902466 A      1/2007
CN     102253080 A     11/2011
(Continued)

OTHER PUBLICATIONS

English Translation of International Preliminary Report on Patentability, WIPO, Geneva, Jun. 2, 2016.
(Continued)

Primary Examiner — Justin N Olamit
(74) Attorney, Agent, or Firm — Bacon & Thomas, PLLC

(57) ABSTRACT

A measuring device which has at least a first component, in which an integral measurement duct is provided or the first component forms in connection with additional components a measurement duct integrally in the measuring device. The measurement duct is provided for conducting a measured medium through the measuring device, characterized in that the first component has a first sensor for determining a first thermophysical property selected from thermal conductivity, thermal diffusivity and/or specific heat capacity of the measured medium, and wherein the measuring device has a second sensor, which vibrates and is provided for determin-
(Continued)

ing viscosity and/or density of the measured medium. The measured medium is conducted through the measurement duct from the first sensor to the second sensor.

28 Claims, 8 Drawing Sheets

(51) Int. Cl.
*G01N 9/00* (2006.01)
*G01N 11/16* (2006.01)
*G01F 1/684* (2006.01)

(56) References Cited

U.S. PATENT DOCUMENTS

| | | | | |
|---|---|---|---|---|
| 6,234,016 | B1 * | 5/2001 | Bonne | G01F 1/6845 |
| | | | | 73/204.26 |
| 6,871,537 | B1 | 3/2005 | Gehman | |
| 7,188,519 | B2 * | 3/2007 | Hornung | G01F 1/6845 |
| | | | | 73/204.26 |
| 7,362,105 | B2 | 4/2008 | Eisenschmid et al. | |
| 7,458,265 | B2 * | 12/2008 | Shih | G01N 5/02 |
| | | | | 73/579 |
| 7,647,844 | B2 * | 1/2010 | Kawanishi | G01F 1/684 |
| | | | | 73/202.5 |
| 9,551,702 | B2 | 1/2017 | Djakov | |
| 2002/0194906 | A1 | 12/2002 | Goodwin et al. | |
| 2011/0257898 | A1 | 10/2011 | Ooishi | |
| 2011/0257989 | A1 | 10/2011 | Kumar | |
| 2015/0160200 | A1 | 6/2015 | Djakov et al. | |

FOREIGN PATENT DOCUMENTS

| | | |
|---|---|---|
| DE | 69231977 T2 | 4/2002 |
| DE | 10123920 A1 | 11/2002 |
| EP | 2574918 A1 | 4/2013 |
| GB | 2491806 A | 12/2012 |
| WO | 2012160393 A1 | 11/2012 |

OTHER PUBLICATIONS

International Search Report,, EPO, The Netherlands, Mar. 16, 2015.
German Search Report, German PTO, Munich, Feb. 11, 2014.
"Gas thermal conductivity measurement using the three-omega method," Sebastian Gauthier et al., Sensors and Actuators A: Physical, Elsevier Sequoia S.A. Switzerland, vol. 195, Jun. 2013, pp. 50-55.

* cited by examiner

MEASURING DEVICE AND METHOD FOR DETERMINING A CORRECTED MASS FLOW AND USES OF THE MEASURING DEVICE

TECHNICAL FIELD

The present invention relates to a measuring device and to a method. The invention relates additionally to a series of new uses, in which this type of measuring device has not yet been applied.

BACKGROUND DISCUSSION

Known are a series of sensors, which measure thermophysical properties. Thus, in the publication, Beigelbeck, R., F. Kohl, S. Cerimovic, A. Talic, F. Keplinger, and B. Jakoby. "Thermal property determination of laminarly-flowing fluids utilizing the frequency response of a calorimetric flow sensor," in Sensors, 2008 IEEE, pp. 518-521, IEEE, 2008, a very sensitive sensor is described, which determines thermal conductivity $\kappa$ and thermal diffusivity $\alpha$ based on a mathematical model.

The publication, Kliche, K., S. Billat, F. Hedrich, C. Ziegler, and R. Zengerle. "Sensor for gaseous analysis based on thermal conductivity, specific heat capacity and thermal diffusivity," in Micro Electro Mechanical System (MEMS), 2011 IEEE 24th International Conference, pp. 1189-1192, IEEE, 2011, describes a series of sensors, which are provided for measuring thermophysical properties.

A large number of scientific articles additionally concern the 3-omega method for determining thermal conductivity. This method is explored, for example, in the publication, Gauthier, Sébastian, Alain Giani, and Philippe Combette, "Gas thermal conductivity measurement using the three-omega method." Sensors and Actuators A: Physical (2013).

Vibrating sensors for determining viscosity and density have already been treated in a number of scientific publications.

Micro-cantilevers are described, for example, in the publication, Naeli, Kianoush, and Oliver Brand, "Dimensional considerations in achieving large quality factors for resonant silicon cantilevers in air." Journal of Applied Physics 105, No. 1 (2009): 014908-014908".

Further developed concepts for application of cantilever models in fluids are discussed in the publications, van Eysden, Cornelis A., and John E. Sader. "Frequency response of cantilever beams immersed in compressible fluids with applications to the atomic force microscope." Journal of Applied Physics 106, no. 9 (2009): 094904-094904, and Ghatkesar, Murali Krishna, Ekaterina Rakhmatullina, Hans-Peter Lang, Christoph Gerber, Martin Hegner, and Thomas Braun, "Multi-parameter microcantilever sensor for comprehensive characterization of Newtonian fluids", Sensors and Actuators B: Chemical 135, no. 1 (2008): 133-138.

The publication, Goodwin, A. R. H., A. D. Fill, K. A. Ronaldson, and W. A. Wakeham, "A vibrating plate fabricated by the methods of microelectromechanical systems (MEMS) for the simultaneous measurement of density and viscosity: Results for argon at temperatures between 323 and 423K at pressures up to 68 MPa." International Journal of Thermophysics 27, no. 6 (2006): 1650-1676, describes the application of vibrating plates for determining viscosity and density of some gases by a correspondingly developed mathematical, physical model.

SUMMARY OF THE INVENTION

Starting from this state of the art, it is an object of the present invention to provide a measuring device, which is able to determine a number of properties of the measured medium and at the same time is distinguished by a compact construction.

The object is achieved by a measuring device. Additionally, a method is provided. Additionally, a number of uses of the measuring device are disclosed, for the most part not so far known for this class of measuring device and leading to a technology substitution of other measuring devices.

The object is achieved by a measuring device as defined in claim 1. Additionally, a method is provided as defined in claim 15. Additionally, a number of uses of the measuring device are disclosed, for the most part not so far known for this class of measuring device and leading to a technology substitution of other measuring devices.

The measuring device of the invention includes at least a first component, in which an integral measurement duct is provided or the first component forms in connection with additional components a measurement duct integrally in the measuring device. Integral means in this connection that the material of the component partially or completely bounds the measurement duct. Thus, no measuring tube is necessary. Suitable as first component is preferably a substrate of ceramic or metal.

The measurement duct is provided for conducting a measured medium through the measuring device.

The measuring device includes a first sensor for determining a first thermophysical property selected from the thermal conductivity $\kappa$, the thermal diffusivity $\alpha$ and/or the specific heat capacity $\rho c_p$ of the measured medium.

The sensor can in a first preferred, constructively-simple embodiment have an RTD, a heatable resistance temperature sensor, as heating element. The 3-omega measuring method allows this heating element both to be heated and at the same time measure the temperature of the medium. Thus, in the case of this embodiment, no additional sensor elements are needed for determining of the thermal conductivity $\kappa$, the thermal diffusivity $\alpha$ and/or the specific heat capacity $\rho c_p$ of the measured medium.

In a second embodiment, the sensor can be composed of a heating element and one or more temperature sensor elements, which ascertain the temperature of the medium near the heating element. From the supplied amount of heat and the ascertained temperature, then the sensor can determine the thermal conductivity $\kappa$, the thermal diffusivity $\alpha$ and/or the specific heat capacity $\rho c_p$ of the measured medium.

The second sensor, which vibrates and, consequently, transmits these vibrations into the measured medium, can be composed of different sensor elements. In a preferred variant, one or more cantilever arms can be utilized. However, also a vibrating plate or some other vibrating, flat element can be provided. The second sensor need not absolutely be located on the same component as the first sensor, but, instead, can, for example, also be located on a second component, especially a separate substrate. In order, however, to assure measuring of the same volume of medium, a measurement duct extending from the first to the second sensor should be provided. The measurement duct extends from the first component via downstream components until reaching a second component, on which the second sensor is arranged.

It is, however, metrologically and also manufacturing technologically advantageous, when the two sensors are arranged on one and the same component.

In the case of the aforementioned preferred first and second embodiments, the measuring device is a sensor for determining properties of the medium.

In additional embodiments, the sensor includes at least the sensor elements of the first and/or the second embodiment and at least one additional temperature sensor. The sensor elements of the first and/or second embodiment form together an active sensor element, which is subsequently referred to herein as a heater.

The one or more temperature sensors supplementally forming the heater are passive sensor elements in the sense of the present invention. The one or more additional passive sensor elements enable ascertaining of the thermal mass flow.

The heater, with the heating element and, in given cases, the additional temperature sensor elements, can according to a preferred embodiment of the invention, in such case, be composed of one or more narrow metal strips arranged straight, ring-like or curved on the first component. The same is preferably true for the passive sensor elements.

The shape of the active and/or passive sensor elements can be achieved, for example, through application of a metal layer on the substrate and a thereon following etching procedure, in which the contour of the heating element is formed e.g. by a masking of certain sections.

Optionally, there can be deposited on the heating element also a protective layer, which protects the heating element against damage of a mechanical or chemical nature.

When the measuring device is a thermal mass flow measuring device, the first sensor determines the mass flow of the measured medium through the measurement duct. For this, the first sensor includes preferably, supplementally to the aforementioned sensor elements, of which the heater is composed, also at least one passive sensor element. A more reliable measuring can, however, be performed based on at least two passive sensor elements.

The first sensor ascertains temperature proportional measured values and measured values relative to the fed-in amount of heat. The second sensor can measure, for example, voltage values, from which the oscillation damping of the medium can be ascertained. It is advantageous, when the measuring device has at least one evaluation unit, which, from measured values, which are measured by the first and/or second sensor, determines at least the thermal conductivity $\kappa$, the thermal diffusivity $\alpha$, the specific heat capacity $\rho c_p$, the viscosity $\mu$ and/or the density $\rho$ of the measured medium.

It is especially advantageous, when the measuring device is a MEMS measuring device or a thin film measuring device, wherein the measuring device is embodied especially preferably as a flow measuring device. A MEMS measuring device (micro electromechanical system) or thin film measuring device is distinguished by very low installed heights and a chip construction. A MEMS flow measuring device has preferably dimensions smaller than a wafer. Especially preferably, sizes for a corresponding flow measuring device lie, however, below 5 $cm^2$.

The measuring device can especially be utilized for determining product characteristics of gases or liquids and/or the composition of a gas- or liquid mixture.

Only by the combined ascertaining of product characteristics can an effective correction of a mass flow occur in the case of an unknown medium.

A corresponding method of the invention for determining a corrected mass flow of a measured medium with a measuring device, especially a measuring device according to one of the preceding claims, includes steps as follows:
a) determining a thermal mass flow of the measured medium;
b) determining, by a first sensor of the measuring device, at least one thermophysical property selected from the thermal conductivity $\kappa$, the thermal diffusivity $\alpha$ and/or the specific heat capacity $\rho c_p$ of the measured medium;
c) determining at least the density and/or the viscosity of the measured medium by a second sensor, which vibrates, and
d) correcting the thermal mass flow of the measured medium based on the ascertained thermophysical property of the measured medium and the density and/or viscosity of the measured medium.

The correcting of the thermal mass flow can preferably occur by means of at least one evaluation unit.

An especially preferred method for operating the measuring device will now be described.

The preferred method is a method for operating a measuring device, especially a flow measuring device, for determining concentration, volume fraction, mass fraction and/or partial pressure of at least one component in a multicomponent, measured medium,
wherein the measuring device has at least
A a first sensor (11, 31, 41) for determining a first thermophysical property, selected from thermal conductivity $\kappa$, thermal diffusivity $\alpha$ and/or specific heat capacity $c_p$ of the measured medium, and
B a second sensor (12) for determining viscosity $\mu$ and/or density $\rho$ of the measured medium (M).

The preferred method is characterized by steps as follows:
a) providing information regarding type of possible components of the measured medium;
b) providing data sets relative to fluid properties, namely viscosity, density, thermal conductivity, thermal diffusivity, specific heat capacity and/or values capable of being derived therefrom for individual components and/or component mixtures and corresponding with the fluid properties determined by the first and second sensors;
c) ascertaining measured values of the first and the second sensors, with which at least two fluid properties of the multicomponent, measured medium are derivable, especially calculatable, wherein a first fluid property is selected from viscosity of the measured medium and density of the measured medium and a second fluid property is selected from thermal conductivity of the measured medium, thermal diffusivity of the measured medium or specific heat capacity of the measured medium
d) ascertaining concentration, mass fraction, volume fraction and/or partial pressure of at least one component of the multicomponent, measured medium based on the measured values or at least two of the fluid properties ascertained therefrom and the data sets.

Individual steps and embodiments of the preferred method will now be explained in greater detail.

In an especially preferred method for operating a measuring device, especially a flow measuring device, the determining of concentration, volume fraction, mass fraction and/or partial pressure of at least one component can occur in a multicomponent, measured medium. In such case, the measuring device is equipped at least with a first sensor, which is suitable for determining a first thermophysical property selected from thermal conductivity $\kappa$, thermal diffusivity $\alpha$ and/or specific heat capacity $c_p$ of the measured medium, as well as with at least a second sensor, which is provided for determining viscosity $\mu$ and/or density $\rho$ of the measured medium.

The especially preferred method can comprise a number of method steps, which need not absolutely occur in alphabetic sequence, especially in the case of steps a) and b).

In step a), preferably a providing of information regarding the types of the possible components of the measured medium can occur. In such case, all relevant components can be input. In case a component is not contained in the measured medium, then its part amounts to "zero" and its concentration is correspondingly output. Ideally known to the user, however, is the complete number of components and their types. In case there is present in the measured medium a component, for which no information is present regarding its type, then, in given cases, an incorrect interpretation regarding the data sets can result.

In step b), data sets are provided relative to fluid properties, namely viscosity, density, thermal conductivity, thermal diffusivity, specific heat capacity and/or values derivable therefrom for individual components and/or component mixtures, which correspond with the fluid properties, which are determined by the first and second, sensors. Derivable values in this context are both values, respectively physical variables, which can be calculated from one or more known fluid properties, and, in given cases, by applying constants. Derivable values can also be directly measured voltages, amplitudes and the like, from which the fluid properties are determinable. This means that it is not absolutely necessary to store in the database the aforementioned fluid properties. Instead, values already converted into the measured variable can also be stored. Since the fluid properties are calculatable from the measured variables (voltage values, etc.), it is possible from the known (predetermined) fluid properties of the individual components in the case of known parameters (e.g. measuring tube radius, etc.) also by means of algorithms to calculate the theoretical values for particular measured variables and to store such as a data set.

Thus, in the following step, for example, either the measured and theoretical fluid properties can be compared or the measured and theoretical values of the measured variables can be compared.

In step c), the first and second sensors ascertain measured values, with which at least two fluid properties of the multicomponent, measured medium are derivable, especially calculatable, wherein a first fluid property is selected from viscosity of the measured medium and density of the measured medium and a second fluid property is selected from thermal conductivity of the measured medium, thermal diffusivity of the measured medium or specific heat capacity of the measured medium.

The ascertaining comprises, in such case, in the case of known process parameters, the active registering, respectively measuring, of measured values for the corresponding measured variables and, in given cases, their conversion into fluid properties.

Finally, there occurs in step d) the ascertaining of concentration, mass fraction, volume fraction and/or partial pressure of at least one component of the multicomponent, measured medium based on the measured values or at least two of the fluid properties ascertained therefrom and the data sets. This can occur by a comparison, e.g. by comparison operations, or calculating or in some other manner.

The aforementioned preferred method for operating the measuring device can additionally be supplemented by other embodiments and/or method steps. Thus, it is e.g. advantageous when in step c) measured values are ascertained, on the basis of which at least three of the fluid properties are derivable and that in step d) the ascertaining occurs with the data sets based on these measured values or at least the three fluid properties. In this way, the determining is more exact, especially in the case of increasing number of components.

The aforementioned method can be applied especially for concentration measurement of individual components of gas mixtures, especially for binary, ternary or quaternary gas mixtures. Also, liquid mixtures, solutions, e.g. salt solutions, and the like can be determined, however, the measurement uncertainty increases. Likewise an option is to determine the concentrations of individual components of gas mixtures having greater than 4 components, wherein, however, also in such case, the measurement uncertainty and the chance of an incorrect association of the measurement results with a data set rises with the number of components.

In order further to lessen corresponding measurement uncertainties and possible incorrect associations, it is advantageous when in step c) measured values are ascertained, on the basis of which at least four of the fluid properties are derivable and that in step d) the ascertaining occurs based on these measured values or at least the three fluid properties are compared with the data sets. For this in concrete examples of embodiments, corresponding sensors, respectively measuring transducers, in compact embodiment are provided, which can be operated according to the method.

The temperature of the multicomponent medium can advantageously be ascertained and taken into consideration in calculating concentration, mass fraction, volume fraction or partial pressure of the at least one component of the multicomponent, measured medium. Thus, it is, for example, possible to provide a correction algorithm for the temperature related changes of the fluid properties or, however, to furnish data sets for different temperature ranges in the database. Pressure can be handled analogously.

The ascertaining in step d) can occur especially advantageously by a comparison of the data sets with the measured values or at least two of the fluid properties ascertained therefrom from step c). The data sets can be furnished in a memory unit as a database for a plurality of components and component mixtures. In such case, it is, however, not absolutely necessary that this memory unit be part of the evaluation unit. Likewise, the evaluation unit can be embodied separately from the measuring transducer. As a result, individual parts of the measuring device need not absolutely be in one structural unit, but can, instead, communicate with one another, e.g. via wireless or other communication paths.

It is advantageous when the aforementioned preferred method includes for concentration additionally other steps as follows:

providing data regarding at least one limit value of a concentration, partial pressure, mass fraction or volume fraction of a component; and outputting an indication in the case of exceeding and/or subceeding the limit value.

Thus, the measuring device can have an additional operating mode. In such case, first of all, a limit value, e.g. a concentration upper limit, of a material component, is predetermined. This limit value can, depending on application, output an indication upon a subceeding or exceeding. The indication can, among other things, be a control command for opening a valve. This is e.g. the case, when a predetermined yield, thus an amount of product, has been achieved in the case of a synthesis reaction. Alternatively, a subceeding of a limit value, e.g. of a starting material, can display that more of this starting material must be fed to the synthesis, in order to establish a chemical equilibrium. In such case, the control command can operate a corresponding valve. A second opportunity for an indication would be a warning. When it theoretically is not possible that a component exceeds or subceeds a certain limit value and the measuring device detects such a change in spite of this, then this can be an indication of an incorrect association of a data set with a composition of the medium.

The present method aims to determine concentration, volume fraction, mass fraction and/or partial pressure of at least one component or, in given cases, a plurality of components in a multicomponent, measured medium. This data can be forwarded for further processing e.g. to a computer system, which can utilize this data, for example, for process control. For a review of the ascertained data by the end user, it is, however, advantageous when an output, especially a visual display, of the concentration, mass fraction, volume fraction or partial pressure of the at least one component of the multicomponent, measured medium occurs on an output unit.

It is additionally advantageous to measure other measured values or one or more other fluid properties, especially the velocity of sound, which enable determining the concentration, mass fraction, volume fraction and/or partial pressure of one or more components, and to provide such to the evaluation unit.

An advantageously embodied measuring device can comprise at least

A a first sensor (11, 31, 41), for determining a first thermophysical property selected from thermal conductivity $\kappa$, thermal diffusivity $\alpha$ and/or specific heat capacity $\rho c_p$ of the measured medium, and B a second sensor (12) for determining viscosity $\mu$ and/or density $\rho$ of the measured medium (M).

Additionally, the measuring device can have an evaluation unit, which is embodied for ascertaining concentration, volume fraction, mass fraction or partial pressure of at least one component of a multicomponent, measured medium.

The evaluation unit can preferably have a memory unit or communicate with such. Stored in this memory unit are data sets, which in cooperation with the measured values of the first and second sensors enable an ascertaining of concentration, volume fraction, mass fraction or partial pressure of at least one component of a multicomponent, measured medium. This can occur, for example, by means of a computing unit, which is part of the evaluation unit.

DETAILED DISCUSSION IN CONJUNCTION WITH THE DRAWINGS

FIGS. 1-6 show an example of an embodiment of a first mass flow measuring device 1 of the invention. In this example, the mass flow measuring device 1 includes a first component 2, which is embodied in compact manner as a monolithic component. This monolithic component is preferably a multi-ply chip, into which the respective functional plies are introduced by means of an etching method.

The mass flow measuring device 1 includes, moreover, a second component 3, which is superimposed on the first component 2 and connected with such. The connection between the first and the second component 2 and 3 is, in such case, preferably pressure stable, especially at pressures greater than 3 bar, and has likewise preferably a good temperature fluctuation resistance at temperature differences of preferably greater than 100 K.

The first component 2 can be utilized as substrate material and be a ceramic, metal or plastic material, wherein the coefficient of thermal expansion of the aforementioned material lies preferably near the coefficient of thermal expansion of the material of the second component. Especially, quartz or silicon can be used. Correspondingly, suitable material combinations are sufficiently known to those skilled in the art from the field of MEMS technology.

Figure 9:
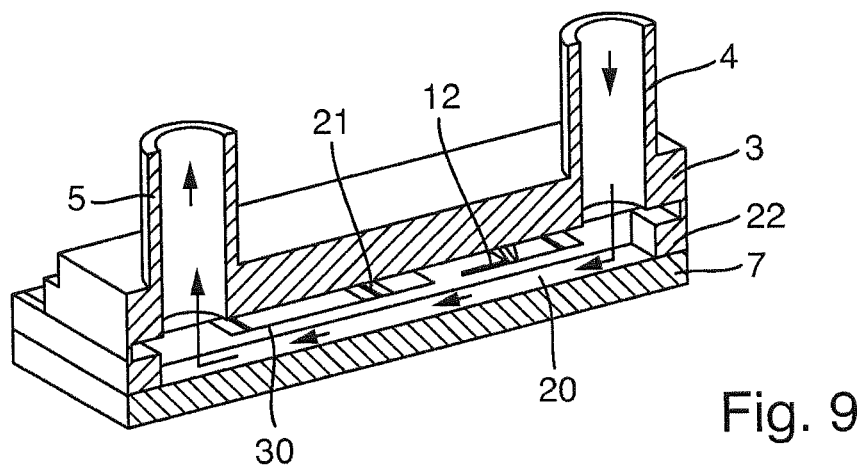
FIG. 9 is a sectional view of the second mass flow measuring device.

The first component 2 forms in connection with a third component 7 and with the second component and integrated in the mass flow device 1 a measurement duct, which is embodied analogously to the measurement duct 20 illustrated in FIG. 9 and through which a medium M to be measured is conducted to and past sensors 11 or 31 and 12. Sensors 11 or 31 and 12 are arranged in the present example of an embodiment on one and the same, first component 2. It is, however, also an option within the scope of the invention to have the sensors arranged on a plurality of components. The measurement duct includes a medium supply 4 and a medium drain 5, with which a measured medium M is fed to or removed from the measurement duct 20. Medium supply 4 and medium drain 5 are arranged on the second component 3.

Figure 1:
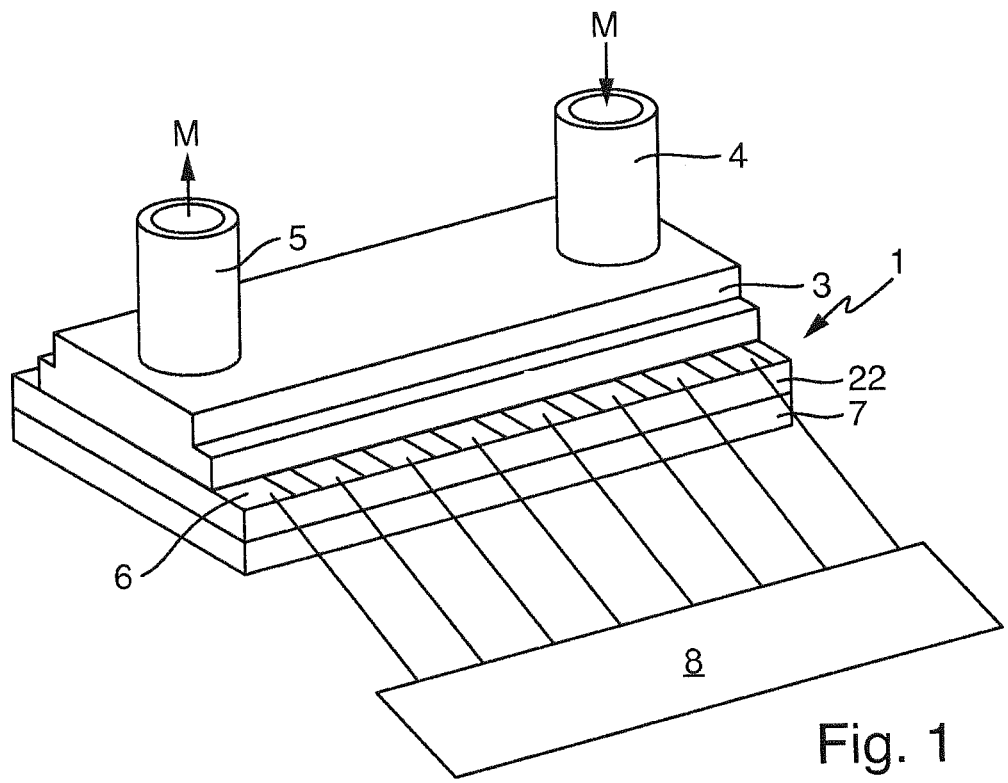
FIG. 1 is a perspective view of a first mass flow measuring device of the invention.

The second component and the third component can be of the same material as the first component. In such case, the third component 7 is connected with the first component 1 likewise pressure resistantly and temperature stably. Evident from FIG. 1 is that the surface of the first component 2 has contacts 6. The surface of the first component 2 protrudes laterally from beneath the second component 3, so that the contacts 6 are accessible. Connected to these contacts can be lines leading to an evaluation unit 8 of the mass flow measuring device 1. This is indicated in FIG. 1 only schematically. The evaluation unit performs the determining and calculating of the output values concerning the properties of the measured medium and the mass flow from the values measured by the sensors 11 or 31 and 12.

Figure 2:
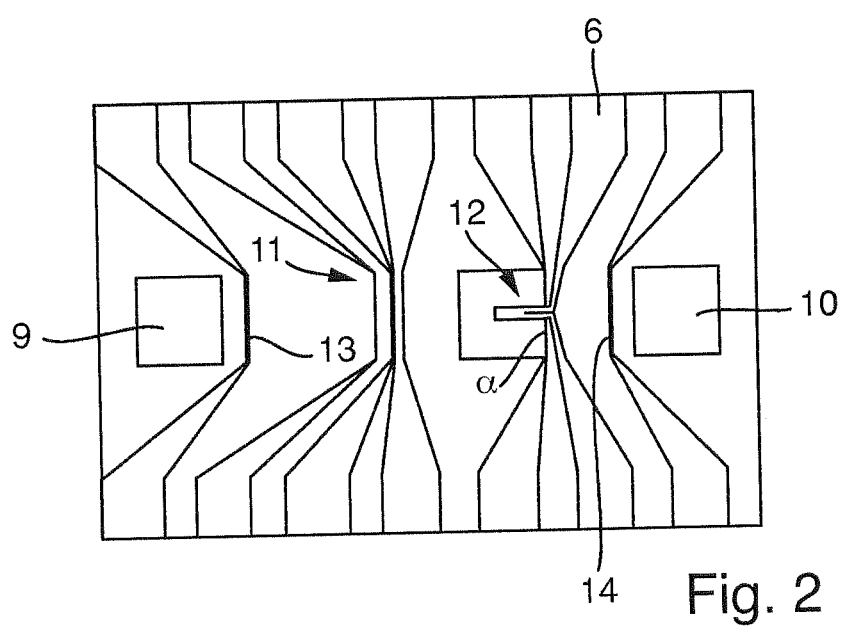
FIG. 2 is a plan view of a first component of the mass flow measuring device of the invention.
Figure 3:
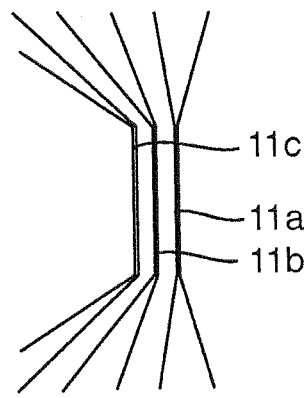
FIG. 3 is a detail view of a first sensor for determining thermophysical properties of a measured medium.
Figure 4:
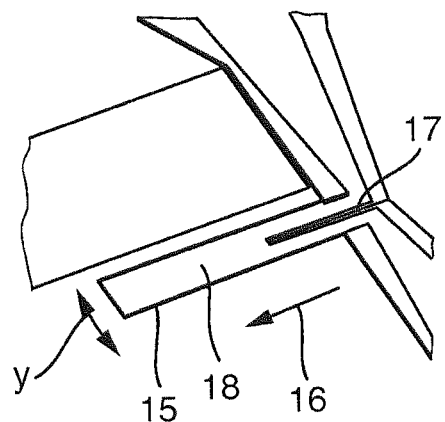
FIG. 4 is a detail view of a second sensor, which vibrates and is arranged on the first component.
Figure 5:
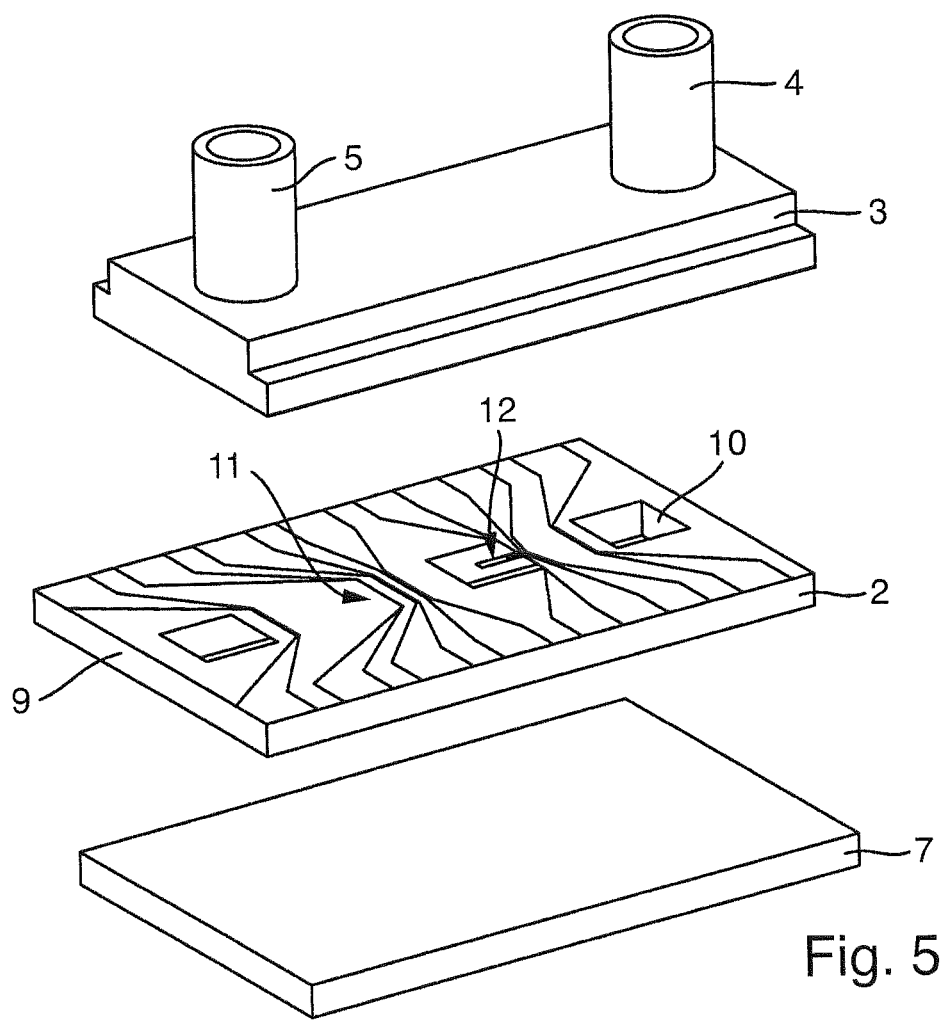
FIG. 5 is an exploded view of the mass flow measuring device.
Figure 6:
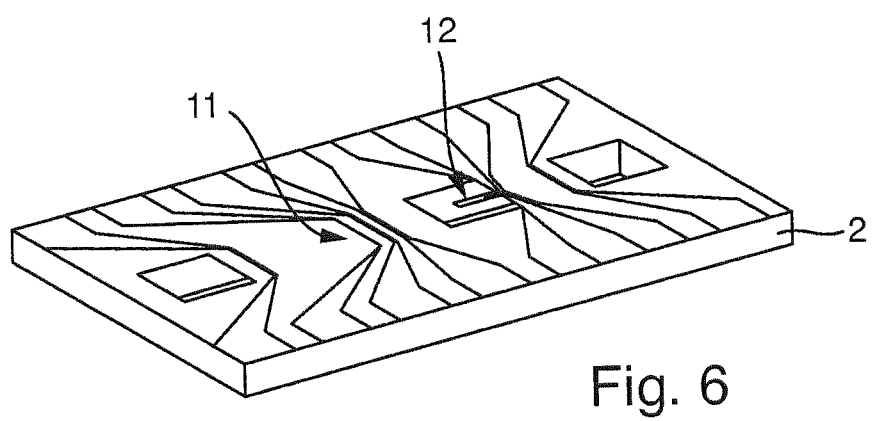
FIG. 6 is a perspective view of the first component.
Figure 7:
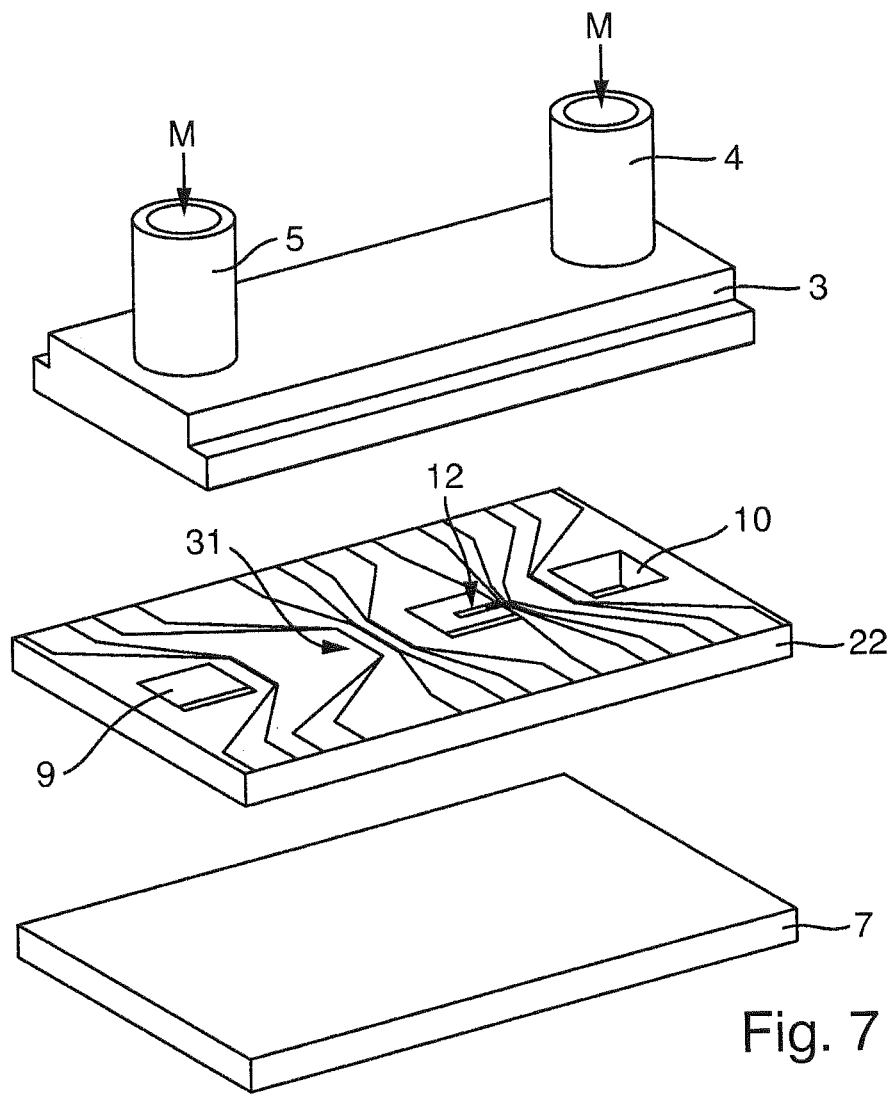
FIG. 7 is an exploded view of a second mass flow measuring device of the invention.
Figure 8:
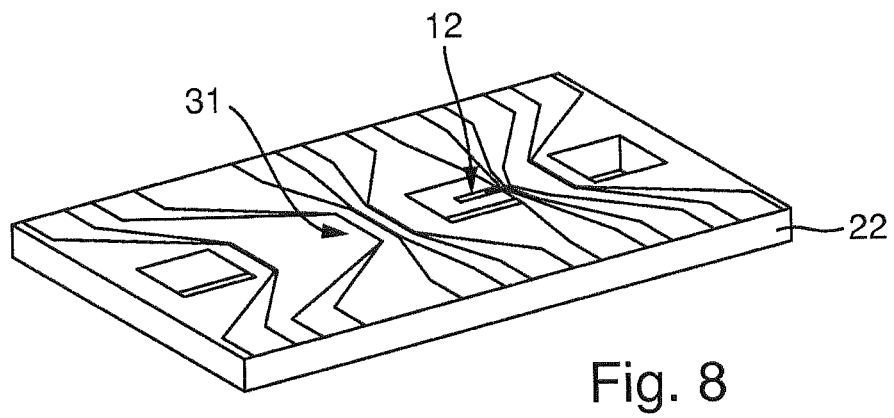
FIG. 8 is a perspective view of a first component of the second mass flow measuring device.

FIG. 2 shows a plan view of the upper side of the first component 2. The rear side of the component includes a formation for the measurement duct. One can see the openings 9 and 10 leading to the measurement duct. The measured medium M moves through the openings 9 and 10 into and out of the measurement duct located below the first component 2. The measurement duct is formed in the first component, for example, by milling or etching, so that the sensor elements 11 or 31 and 12 stand in direct contact with the measured medium or are protected by a thin material ply against chemical or mechanical damage. Alternatively, the measurement duct can also be formed in the second component 3, so that the medium is led from the side of the second component 3 over the sensors 11 or 31 and 12.

The first component 2 includes at least a first sensor 11 or 31. This sensor 11 or 31 serves for ascertaining the thermophysical properties of the medium. An example of such a property is the thermal conductivity of the medium. It can, however, supplementally also be the thermal diffusivity of the medium. In the case of ascertained or predetermined density, also the specific thermal conductivity can be ascertained by the sensor.

The mass flow measuring device 1 includes additionally at least a second sensor 12. Sensor 12 vibrates and permits other properties of the medium to be ascertained, preferably the density and the viscosity.

The aforementioned second sensor 12 can especially preferably be provided together with the first sensor 11 or 31 in one and the same component 2. This assures simple manufacture and compact construction of the mass flow measuring device. Miniaturized mass flow measuring devices are implementable thereby. In such case, the medium duct is not formed by a measuring tube, but, instead, it is an integral component of the mass flow measuring device. The means the medium duct is in the material of one of the components 2 or 3, especially in the material of the second component 2, or it is embodied by bringing together a of plurality components, here the first, second and third components 2, 3 and 7.

The flow measuring device shown in FIGS. 1-6 combines a first sensor 11 or 31 for determining thermophysical properties of a measured medium with a second vibrating sensor 12 functioning as a viscometer.

Appropriate vibrating sensors can preferably be embodied as cantilevers. Cantilevers working according to the principle of a viscometer are already known per se. A cantilever is an extension, respectively a projecting segment, which is caused to vibrate. The vibrations can be produced by piezoelectric excitation, electromagnetic excitation or electrostatic excitation.

Vibration viscometers operate according to the principle of the damping of an oscillating electromechanical resonator, which is held in a medium, whose viscosity is to be ascertained. The resonator, in such case, emits transverse oscillations or oscillations produced by torsion. The transverse oscillations can be produced by the cantilever arm illustrated in FIG. 4. The higher the viscosity, the higher is the damping of the resonator. The damping of the resonator can be measured in different ways. Thus, the supplied power can be ascertained, which is required, in order to be able to oscillate the resonator at a constant amplitude. Also the time delay of the signals can be ascertained, when the resonator is turned off. Another opportunity for the measuring is ascertaining the frequency of the resonator as a function of a phase angle between excited and received waveforms. The higher the viscosity, the higher is the frequency change for a given phase change.

In addition to viscosity, the cantilever can also be used to determine density of the measured medium. Thus, the vibrating sensor ascertains also physical properties of the measured medium. As shown in FIGS. 1-6, an option is to arrange the first and second sensors on one and the same monolithic chip. This chip can be executed in MEMS construction (micro electromechanical systems).

In the special examples of embodiments in FIGS. 1-10, the exciting of the cantilever 18 is produced by an electromagnetic excitation by means of a magnetic field, e.g. an axial magnetic field, preferably produced by a coil (not shown in detail) or at least one permanent magnet. Corresponding coils, which e.g. are present printed on a circuit board are known e.g. from DE 10 2012 102 979 A1. The construction of the cantilever is shown in detail in FIG. 4. Shown are an AC conductor loop 15, which is preferably arranged on the outside of the cantilever and a magnetic field 16 directed perpendicularly thereto. If, now, a measured medium, for example, an electrically-conducting medium, flows past the cantilever 18, then the cantilever is caused to oscillate. The cantilever includes additionally a resistor 17, preferably a piezoresistor, which, depending on amplitude, changes the oscillations of the cantilever arm. The piezoresistor can preferably be embodied as a one-piece element, e.g. as a one-piece bridge, or as a bridge with four piezoresistive resistors. By AC excitation, the cantilever arm is caused to execute Y oscillations. These oscillations are differently strongly damped, depending on the viscosity of the measured medium. This damping can be registered via the piezoresistor. This principle is shown in detail in FIG. 4.

The cantilever is, in such case, arranged in a rectangular free space and is mounted with its side wall a toward the first component.

Using the mass flow device, at least five physical properties of the medium can be ascertained. These are especially the thermal conductivity $\kappa$, the thermal diffusivity $\alpha$, the viscosity $\mu$, density $\rho$ and the specific heat capacity $\rho c_p$ of the medium. By means of these variables, thermal mass flow can be ascertained and disturbances partially or completely compensated.

Figure 12:
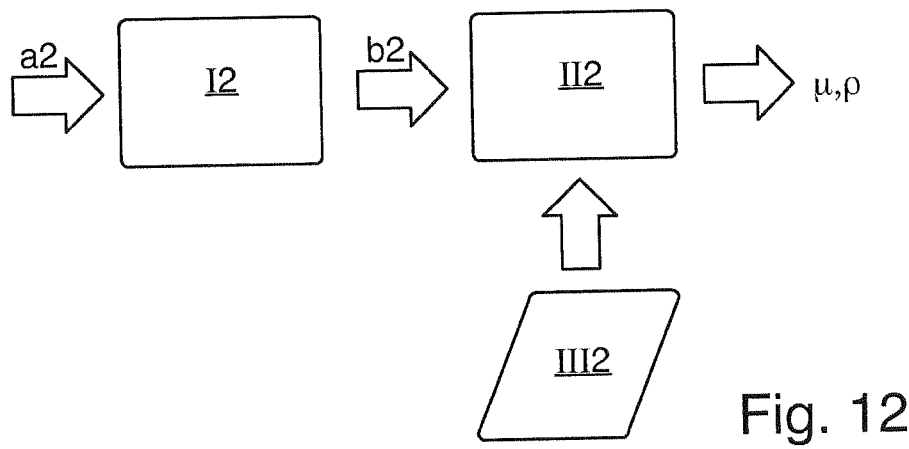
FIG. 12 is a flow diagram for how the second sensor works.

The measuring method of the second sensor is illustrated in FIG. 12. The second sensor I.2 is, in such case, in an excitation step a2, caused to oscillate by, for example, an electromagnetic excitation. These oscillations are introduced into the measured medium and, depending on properties of the measured medium, measured values are ascertained as response to the excitation. The measured values, for example, in the form of a voltage signal b2 as a function of the damping characteristics of the medium on the oscillations, can be converted by the evaluation unit II.2 with the aid of a mathematical-physical model III.2 into physical variables for describing the properties of the thermophysical measured medium. These are the viscosity and/or density of the measured medium.

The first component 2 includes additionally a metal ply 30. This is smaller than 10 µm, preferably, however, less than or equal to 6 µm. Formed from this film are individual segments of the first and/or second sensor 11 or 31 and 12 as well as their contacts 6. The arrangement of the sensors was so optimized to the requirements that they are integrateable easily into a flow measuring device with an integrated measurement duct. Especially in the small-dimensioned ranges of flow measuring devices, such optimized arrangements are advantageous in the case of measuring microfluids.

Besides a cost-saving, also a faster measuring can occur in the case of one or more changing media or a changing composition of the medium.

A corresponding sensor can preferably have a medium facing surface of less than 10 cm$^2$ and a sensor thickness of less than 0.5 cm. The measurement duct has, in such case, preferably an average diameter of less than 2 mm.

The flow measuring device is embodied as a thermal mass flow measuring device. In such case, the first sensor 11 enables the ascertaining of the mass flow. For this, the sensor includes various sensor elements.

Thermal flow measuring devices use usually two heatable sensor elements, which are embodied as equally as possible and which are in thermal contact with the medium flowing through the measurement duct 20. One of the two sensor elements is a so-called active sensor element, which is heated by means of a heating unit. This active sensor element is subsequently referred to as heater 11*b*, 21. Provided as heating unit is either an additional resistance heating element, or the sensor element itself is a resistance element, e.g. an RTD (Resistance Temperature Device) sensor, which is heated by conversion of electrical power, e.g. by a corresponding variation of the measuring electrical current. The second of the two sensor elements is a so-called passive sensor element 11*a*, 11*c*, 23 and 24: It measures the temperature of the medium and is preferably arranged in the vicinity of the active sensor element, the so-called heater. Moreover, also a third sensor element can be provided as a passive sensor element, which likewise is arranged in the vicinity of the heater. Ideally, consequently, a sequence of the sensor elements is provided in the flow direction, wherein the sequence is composed of the second sensor element 11*a*, 24, the heater 11*b*, 21 and the third sensor element 11*c*, 23. Thus, the passive sensor elements are positioned in the flow direction on both sides of the heater 11*b*, 21. The passive sensor elements can be arranged symmetrically, thus at the same separation from the heater. Especially advantageous, however, is an asymmetrical arrangement of the two passive sensor elements relative to the heater. In order to obtain a higher sensitivity, also thermistors can be used as passive sensor elements. The heater, respectively its individual elements, can preferably be made of chromium, nickel and/or platinum. There are, however, also other known materials, which can serve as heatable elements.

Usually in a thermal flow measuring device a heatable sensor element is so heated that a fixed temperature difference is maintained between the two sensor elements. Alternatively, it is also known to employ a control unit to supply a constant heating power.

If there is no flow in the measurement duct 20, then a constant amount of power is required for maintaining the predetermined temperature difference. If, in contrast, the medium to be measured is moving, then the cooling of the heated sensor element is essentially dependent on the mass flow of the medium flowing past. Since the medium is colder than the heated sensor element, heat is transported away from the heated sensor element by the flowing medium. In order thus in the case of a flowing medium to maintain the fixed temperature difference between the two sensor elements, an increased heating power is required for the heated sensor element. The increased heating power is a measure for the mass flow, respectively the mass flow of the medium through the measurement duct.

If, in contrast, a constant heating power is supplied, then the temperature difference between the two sensor elements lessens as a result of the flow of the medium. The particular temperature difference is then a measure for the mass flow of the medium through the measurement duct.

There is, thus, a functional relationship between the heating energy needed for heating the sensor element and the mass flow through a pipeline, respectively through the measurement duct. The dependence of the heat transfer coefficient on the mass flow of the medium through the measuring tube, respectively through the pipeline, is utilized in thermal flow measuring devices for determining the mass flow.

From the closeness of the second and third sensor elements 11*c* and 11*a* to the heater 11*b*, it is additionally possible to ascertain a flow profile.

In addition to the two sensors 11 or 31 and 12, the flow measuring device optionally includes a third and/or a fourth sensor 13, 14. These optional third and fourth sensors can be made, for example, of nickel. In the present example of an embodiment, the two sensor elements 13 and 14 are arranged spatially separated from one another on the first component 2 in the regions of the medium drain 5 and the medium supply 4. They measure the temperature of the medium without influence of the heat input from the heater 11*b*, 21.

Figure 11:
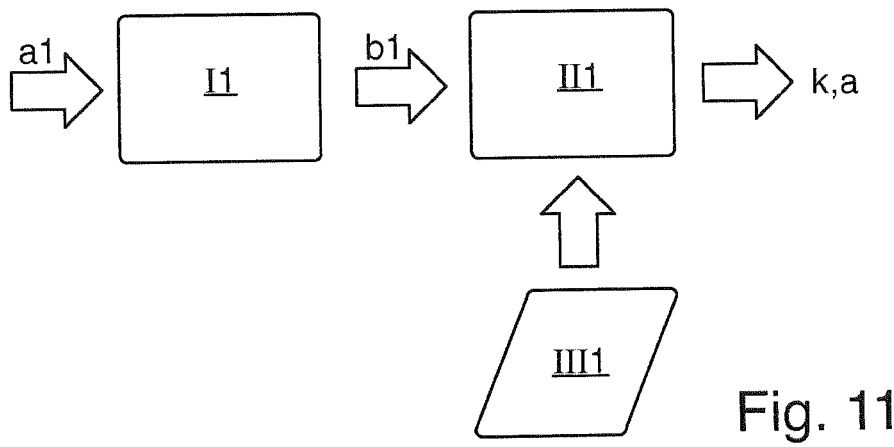
FIG. 11 is a flow diagram for how the first sensor works.

An illustration of the measuring method is shown in FIG. 11. The heater is, in such case, excited in an excitation step a1 with an AC and DC signal. The heater is introduced into the measured medium and, depending on properties of the measured medium, measured values are ascertained as response to the exciting. This is done by the first sensor I.1. The measured values in the form of a temperature signal b1 with amplitudes and phases, more exactly stated with the amplitude and the phase of a temperature signal, are converted by the evaluation unit II.1 with the aid of a mathematical-physical model III.1 into physical variables for describing the properties of the thermophysical, measured medium. These are the thermal conductivity and/or the thermal diffusivity.

The temperature of the medium is ascertained both at the passive sensor elements 11*a*, 11*c*, 23, 24 and/or at the heater 11*b*, 21 as resistance values or as voltage values. These temperature measurement points of the temperature signal vary and have, consequently, an amplitude and a phase. The phase is to be viewed as a time shift, wherein the T signal remains the same. This behavior of the temperature signals results in periodic curves, brought about by the AC excitation of the heater.

Based on the amplitudes and phases of the temperature signals and the system construction, the thermal conductivity and the thermal diffusivity of the surrounding medium can be ascertained. This happens as a function of dimensioning of the sensor and the individual sensor elements relative to one another. Thus, an especially preferred arrangement of the sensor elements relative to one another contributes to a better ascertaining of the aforementioned thermophysical parameters.

The two examples of embodiments of FIGS. 1-4 and FIGS. 5-8 are identical in a number of features. The difference between the two examples of embodiments results mainly from the shaping and manner of operation of the first sensor, which is utilized for determining the thermophysical properties.

The two embodiments show, respectively, embodiments of sensors for mass flow measuring devices. The sensors can, however, also be utilized for pure property determination of a medium. The matter of operation will now be described in greater detail relative to the first sensor 11 or 31, which is applied for ascertaining the thermophysical properties.

The first sensor shown in FIGS. 1-6 can be described as a sensor 11 with a temperature dependent heater. This works as a thermometer. In this arrangement, the heater 11b includes a heating element, which at the same time performs a temperature measurement at the third frequency. The AC response of the heater, the thermal conductivity κ and the specific heat capacity $\rho c_p$ of the medium can be determined. This can occur using the 3-omega method.

The 3-omega method is a measuring method for determining the thermal conductivities of media, especially gases or liquids. In such case, the heater 11b applied on the first component is periodically heated and the temperature oscillations arising thereby measured. The thermal conductivity and thermal diffusivity of the measured medium can be determined from their frequency dependence.

The 3-omega-method is known per se. A signal- and/or energy transmission can occur at three different frequencies.

Starting from the 3-omega method, an electrical current or an electrical current equivalent voltage can be transmitted at one frequency for operating the heating element.

A second frequency can transmit the transferred heat or the power required therefor.

The measured temperature can be transmitted at a third frequency.

$$V(t) = I(t) * R(t) = I_0 * R_0 * \left[ \cos\left(\frac{1}{2} * w * t\right) + \left(\frac{1}{2} * \alpha * T_w * \cos\left(\frac{1}{2} * w * t - \varphi\right) + \frac{1}{2} * \alpha * T_w * \cos\left(\frac{3}{2} * w * t - \varphi\right) \right) \right]$$

wherein ω represents the angular frequency and $I_0$ the supplied electrical current level. t is the heating duration and φ the phase shift. $T_w$ describes the amplitude of the temperature at the measuring point. From this formula comes the third harmonic.

In the present case for the embodiment of the sensor in FIGS. 1-6, the temperature difference ascertainment of the temperature sensors str can occur based on the DC signal, which can be utilized for calculating the flow and/or the flow velocity of the medium according to the calorimetric measuring principle.

In the case of FIGS. 7-10, the heater 21 works temperature independently. It is composed of a heating element 21A, 21B, 21C and one or more temperature sensor elements 21D. The heating element 21 can, in such case, not function alone as a sensor, but, instead, only in connection with the additional temperature sensor element 21D. In this case, one can see from FIG. 10A that the heating element is arranged around the temperature sensor element. The heating element can be composed of two elongated segments 21an and 21c and a bridge 21b, such as is likewise shown in FIG. 10A.

This arrangement enables the temperature sensor element 21D to ascertain the temperature of the medium as near as possible to the heating element. As already explained, the AC response of this temperature sensor element 21D is utilized for determining the thermal conductivity κ and the specific heat capacity $\rho c_p$ of the medium. Although this arrangement appears firstly complex in its manufacture compared with the variant of FIGS. 1-6, it offers the advantage of a smaller measuring complexity, since frequency is lower in the case of this arrangement. Since the AC signal at the excitation frequency (omega) can be utilized for measuring, this signal is, moreover, stronger than the signal of the 3-omega method.

The flow can be determined as in the preceding example by ascertaining the temperature difference based on the passive sensor elements 23 and 24 arranged upstream and downstream of the heater 31. The heater 21 and the two passive sensor elements 23 and 24 form, in this case, together the first sensor 31.

In such case, the ascertaining of the flow occurs based on the DC measurement signal based on the calorimetric measuring principle.

Other alternative arrangements of the individual sensor elements, thus the passive sensor elements and/or the heater, are possible and can be embodied by corresponding designs.

Figure 13:
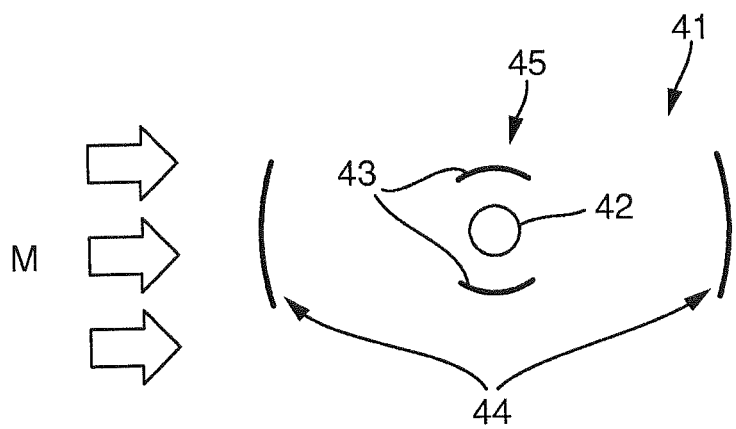
FIG. 13 is a detail view of an arrangement of sensor elements of a first sensor of a third mass flow measuring device.

An alternative example of an embodiment for a corresponding design variation is shown in FIG. 13.

FIG. 13 shows schematically an alternative first sensor for a mass flow measuring device. This sensor includes an annular heating element 42 as part of a temperature independent heater 45. This heater 45 includes supplementally to the heating element 42 two arc shaped temperature sensor elements 43. Also in this case, the temperature sensor elements 43 of the heater 45 are arranged very near to the heating element 42. As a result, the heater as an active sensor element is also, in this case, constructed of a heating element and one or more temperature sensor elements. The heater serves, in such case, for determining the already mentioned, thermophysical properties of the medium. The temperature sensor elements 43 are asymmetrically positioned, vertically to the flow direction and near to the heating element 42, in order to lessen, as much as possible, the influence of the flow on the measuring. By measuring the amplitude and the phase of the AC temperature signal, a calculation of the thermal conductivity and the specific heat capacity of the medium can occur.

Moreover, the first sensor includes, supplementally to the heater 45, two arc shaped passive sensor elements 44. These serve for determining the flow velocity or the flow of a measured medium M. The sensor elements 44 arranged upstream and downstream from the heater 45 enable the determining of the flow and/or the flow velocity.

Figure 10:
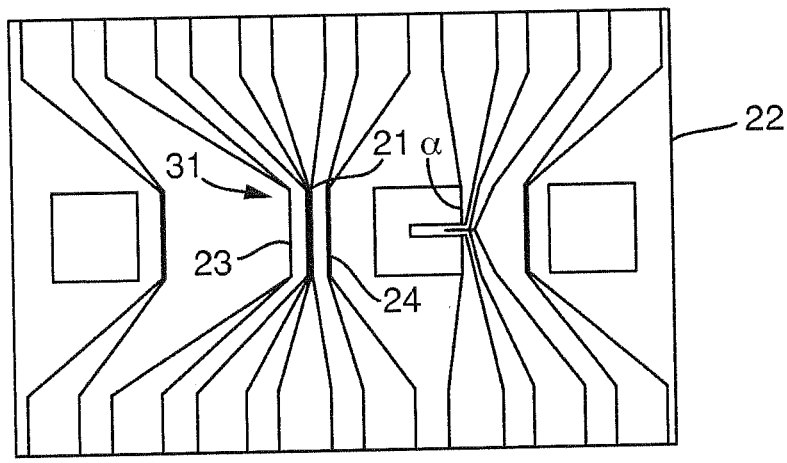
FIG. 10 is a plan view of the first component of the second mass flow measuring device.
Figure 10A:
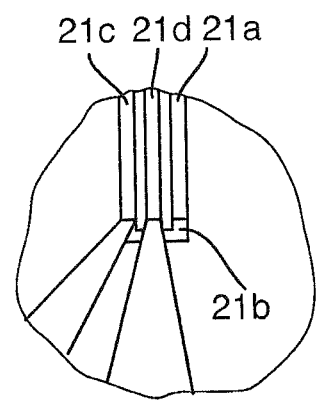
FIG. 10A is a detail view of a first sensor for determining a thermophysical property.
Figure 14:
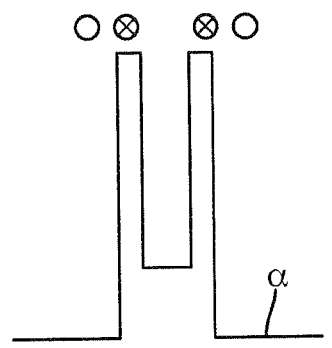
Figure 15:
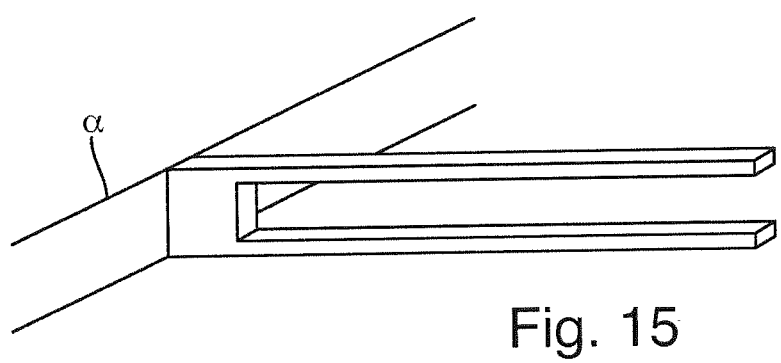
FIG. 15 is a second sensor of a fifth mass flow measuring device.

The second sensor 12 can likewise have different embodiments. FIG. 14 shows two interconnected cantilevers, which can oscillate outside a plane that extends along the longitudinal axis of the sensor and perpendicular to the wall α (such as shown in FIGS. 2 and 10). Alternatively, the cantilever arms can also, such as shown in FIG. 15, be arranged on top of one another, as seen in the side view of the mass flow measuring device, wherein the cantilever is affixed to the wall α, such as shown in FIGS. 2 and 10. In this way, the sensor behaves like a tuning fork. The oscillation excitement can occur by electromagnetic excitation, piezoelectric excitation, thermal excitation (in the case of bipolar behavior) or electrostatic excitation.

Additionally or alternatively to cantilever elements, also planarly vibrating sensor elements can be utilized. These sensor elements can oscillate within the plane of the first component, respectively within the sensor chip plane.

The detecting part of the second sensor can preferably be a piezoresistive element. Other means for detecting the oscillation of the sensor can likewise be used, for example, electrostatic or optical means of detection.

The cantilever arms illustrated in FIGS. 14 and 15 are ideally coupled together in their eigenform. This has the special advantage that no energy losses to the support of the vibrating sensor elements occur.

The method for ascertaining the thermophysical properties is based on the calorimetric principle. This can be achieved, for example, with the above-described embodiment of the first sensor, thus e.g. when a superimposed DC electrical current is fed to the heater.

The calorimetric ascertaining can occur by measuring the amount of heat, which is generated by the heater and by measuring the temperature difference of the passive sensor elements upstream and downstream of the heater.

In such case, the following relationships hold:

| Equation | | principle |
|---|---|---|
| $\overline{T} = f_{th.\ Amp}(k, \rho * c_p)$ | eq. 1 | Thermal sensor amplitude (temperature) |
| $\Delta\varphi_{th} = f_{th.\ Phase}(k, \rho * c_p)$ | eq. 2 | Thermal sensor phase (temperature) |
| $\overline{w} = f_{visc.\ Amp}(\mu, \rho)$ | eq. 3 | Vibrating element amplitude (displacement) |
| $\Delta\varphi_{vib} = f_{visc.\ Phase}(\mu, \rho)$ | eq. 4 | Vibrating element phase (displacement) |
| $\rho u = \dot{Q}_{heater} A c_p \Delta T_{up} - do$ | eq. 5 | Calorimetric principle |

NOMENCLATURE $\mu$ Dynamic viscosity [kg/ms]
$\omega$ Angular frequency [rad/s]
$\varphi$ Phase [rad]
$c_p$ Specific heat capacity
f Frequency [Hz]
k Thermal conductivity [W/mK]
l Characteristic length [m]
$\dot{Q}_{heater}$ Heat flow [W]
$\rho$ Density[kg/m$^3$]
u Flow velocity [m/s]
T Temperature [K]
w Displacement [m]
$\overline{T}$ Temperature amplitude [K]
$\Delta\varphi_{th}$ Temperature phase shift [rad]
$\overline{w}$ Displacement amplitude [m]
$\Delta\varphi_{vib}$ phase shift of vibrating element between excitation and displacement The above relationships provide a system with 5 unknowns to be ascertained, the thermal diffusivity k, the viscosity $\mu$, density $\rho$, the-specific heat capacity $c_p$ of the medium and the velocity. All additional constants are ascertained by measuring or are constants.

Starting from these relationships a gas independent thermal flow measurement is achieved, since a self correction can occur. This is especially advantageous in the case of a medium alternation or in the case of a change of the composition of the medium.

In order to ascertain the mass flow $\rho u$ from the above-mentioned function 5, the heat capacity $c_p$ should be ascertained, in order to achieve a self correcting of the mass flow. This can occur by solution of the functions 1-4. By solving the above mentioned functions, the values of four properties can be ascertained, which provide additional information relative to the measured medium. The equations 1-4 are shown in general form. They describe the frequency response of the first sensor and the second sensor. Various models have been offered by different researchers, in order to ascertain these functions. The different models are explained in greater detail in the above-mentioned scientific articles from the state of the art, wherein reference is expressly taken to these publications in the context of invention.

These complex models can be represented in the above general form.

Figure 16:
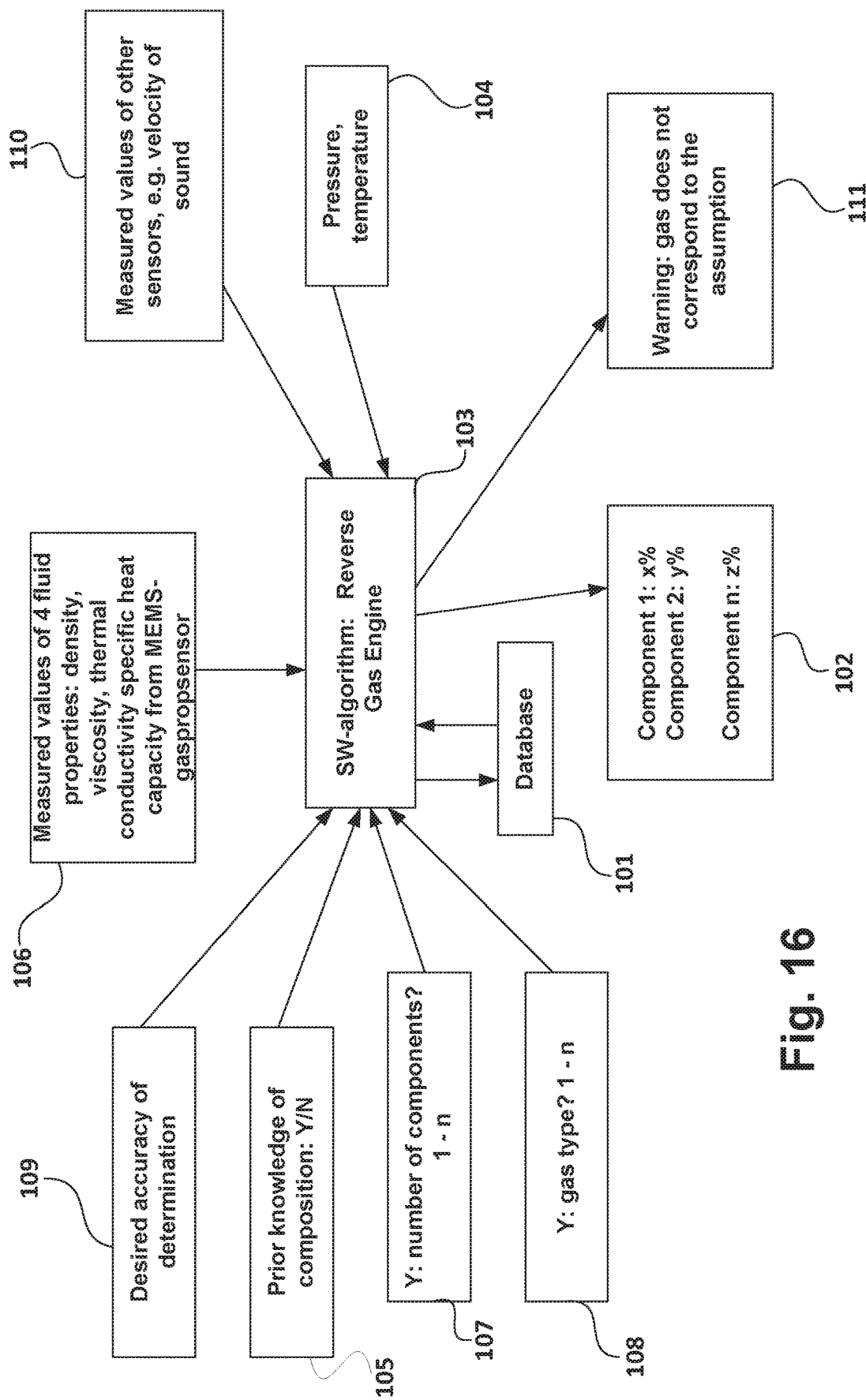
FIG. 16 is a flow diagram showing an embodiment of the manner of operation of a mass flow device of the invention.

The mass flow measuring devices illustrated in FIGS. 1-15 preferably include an evaluation unit (not shown in greater detail). FIG. 16 shows a method schema, which is performable by the evaluation unit. The evaluation unit need not absolutely be mechanically connected with the sensor, but, instead, can also be located separated from such and communicate with such, e.g. by cable connection or wireless connection or the like.

The evaluation unit accesses a database 101. This is stored in a data memory arranged within the evaluation unit. Alternatively, it can also be an external data memory, e.g. in an external server, from which the evaluation unit retrieves the data, respectively with which the evaluation unit communicates.

The evaluation unit can have different operating modes, which will now be explained in greater detail:

A first operating mode enables at least the concentration statement 102, the mass fraction, the volume fraction and/or the partial pressure of a component of a gas- and/or liquid mixture or solutions of at least two or more components.

The evaluation unit includes a computing unit 103, which accesses the aforementioned database. The database includes at least one data set of physical fluid properties for pure gases and/or liquids. These data sets include at least two fluid properties selected from density, viscosity, thermal conductivity and/or specific heat capacity.

It can, however, be expanded to all four aforementioned fluid properties. Moreover, the data set can also include data for the aforementioned fluid properties at different pressures and temperatures 104. Furthermore, also data sets for two- or multicomponent fluid mixtures, thus liquid- and/or gas mixtures or for solutions, e.g. salt solutions, can be furnished. Thus, e.g. in the case of binary gas mixtures, density, viscosity, thermal conductivity, specific heat capacity and/or thermal diffusivity for different mixing ratios, e.g. 1:9, 2:8, 3:7, 4:6 and 5:5 can be given. Of course, analogous data can also be given for ternary or quaternary liquid- and/or gas mixtures.

The sensor ascertained, measured values 106, from which density, viscosity, thermal conductivity, specific heat capacity and/or thermal diffusivity of the fluid mixture are ascertainable, are sent by the sensor to the evaluation unit, converted there into the aforementioned fluid properties and compared with the data sets furnished in the database.

In the case of agreement of the measured values or the therefrom calculated fluid properties with a specific data set, for example, the fraction or the concentration of the components can be given.

The above-described sensors can especially be utilized for gas compositions. Thus, density, viscosity, thermal conductivity and specific heat capacity can be ascertained by one and the same sensor. This makes it especially advantageously possible without supplemental previous knowledge directly to determine the fractions, respectively concentrations of the components.

In case less information relative to the fluid properties is provided by the sensor or in order to enable a more exact determining, then other operating modes can be selected.

A second operating mode enables the taking into consideration of previous knowledge 105. It is, for example, possible to specify in the device from the beginning all or individual relevant gas components of the gas mixture. The evaluation unit can, in this case, only query for the data sets, in which the corresponding gas components are present, whereby the evaluation occurs more exactly and with smaller errors.

A first suboperation mode of the second operating mode enables specification of the number of components 107. In this way, e.g. the evaluation unit can in the case of small disturbances exclude other components in the gas mixture.

A second suboperation mode of the second operating mode enables specification of the type of one or more components 108. The components can be e.g. methane. In this case, only the number of data sets with gas mixtures are downloaded, which have methane as a component.

In an additional operating mode, a user can set a concentration specification 109, for example, a minimum concentration of carbon dioxide. The evaluation unit can be programmed in such a manner that a plausibility inquiry occurs, when the concentration ascertained by comparison of the fluid properties is smaller than the minimum concentration. In this case, this would indicate an error of the measuring and, in given cases, would be output as an error report 111.

With the above-described sensor variants, it is additionally an option to determine the temperature of the fluid mixture. This ascertained temperature can preferably be taken into consideration in ascertaining the right data sets. The same holds for the pressure. For this, for example, an additional pressure sensor can be provided.

The evaluation unit additionally enables process control. Thus, it is possible, for example, to the extent that a first component of a gas changes, also correspondingly to control the concentration of the second component, e.g. via a pressure control valve, in order so to fulfill a preset situation, respectively specification, set by a user concerning the minimum concentration of the second component.

A comparison between fluid properties ascertained from the measured values and the data sets stored in the database is already theoretically possible from two fluid properties on up, wherein the two fluid properties are selected from density, viscosity, thermal conductivity, thermal diffusivity and/or specific heat capacity, or physical variables derivable therefrom.

The corresponding determination of the fractions, concentrations and/or partial pressures can occur both with application of the ideal gas equation or for real gases. In the latter case, mathematical mixing models and corresponding software programs can be utilized, in order to simplify the calculating.

In given cases, for instance for adjustment or for improving accuracy, measured values of other sensors 110, thus e.g. the velocity of sound in the fluid mixture, can be ascertained and taken into consideration in the case of calculating concentration. It is known that individual ultrasonic, flow measuring devices can already determine concentrations of some components. Available from the applicant is, for example, a corresponding measuring device under the designation "Praline Prosonic B200" for biogas measurement.

In the following, some uses of the invention will now be described. In such case, in the respective application of the invention, measuring-, analytical- and/or detection devices can be replaced, which work according to other measuring principles and are partially essentially larger dimensioned, more expensively manufacturable or disturbance susceptible. Alternatively, the measuring device of the invention can also be applied for reviewing the functional ability of measuring devices already customary in the respective applications.

The measuring device can according to the invention be applied for determining concentration of at least one component of a gas mixture with known ingredients. That means that, indeed, in the case of the corresponding gas mixture, it is known which type of components (e.g. $CO_2$, steam, propane) are contained in the gas mixture, however, not to what degree the particular component, e.g. steam, is contained in the gas mixture. Vapors are, in such case, treated in the same way as gases and can be components of the gas mixture.

The aforementioned gas mixture can preferably be a binary and/or ternary gas mixture.

The one component is preferably an aliphatic hydrocarbon with a chain length of less than 4 C-atoms, especially methane. Many measuring devices cannot quantify aliphatic hydrocarbons sufficiently exactly—especially in the presence of carbon monoxide or carbon dioxide. This measurement task can, however, be accomplished in the case of the present new measuring principle.

While so-called "gas analyzers" are embodied to be very large and partially can determine material fractions, in each case, of only one component of a gas mixture, the present measuring device enables determining the concentrations of all components of the ternary gas mixture.

The measuring device can especially be used for determining the methane fraction in a methane containing gas mixture, especially in natural gas, landfill gas, biogas and/or synthesis gas.

According to the invention, the present measuring device can also determine the heating value of a combustible gas mixture, especially a binary or ternary gas mixture. Combustible gas mixtures include also methane containing gas mixtures but are not limited to these. The combustible gas components are also not limited to hydrocarbons as combustible components, but, instead, e.g. also helium, hydrogen, etc. can be present as combustible components in the gas mixture.

The measuring device can be utilized both for detecting and quality testing a gas, e.g. a pure- or very pure gas and, in given cases, simple gas mixtures (e.g. binary gas mixtures). It can also be utilized for quantifying a gas mixture.

Additionally to this qualification as well as also quantifying of the gas, gas mixture or individual components of the gas mixture, the measuring device can be used for control of flow of a measured medium, especially a gaseous medium, wherein the control occurs by means of a control apparatus, wherein the control apparatus is operated as a function of a first thermophysical property and density of the measured medium.

The measuring device of the invention can operate a mass flow controller, which is a variant of the aforementioned control apparatus, or be integrated in such a mass flow controller.

According to the invention, the measuring device can be applied for control of the medium flow, for example controlling the in- and outflow of gases in a burning process of a combustion apparatus, especially the supply of oxygen and combustible gases and/or the outflow of exhaust gases. The means the burning can be set to a predetermined range and, thus, be optimized regarding the thermal output and/or the material consumption. The measuring device can, thus, be applied in a combustion plant.

Alternatively, the combustion apparatus, for whose control the measuring device is applied, can be arranged in an internal combustion engine. The measuring device can, in such case, be applied for optimizing the combustion process in the internal combustion engine, especially in an internal combustion engine of a land- or water vehicle. Thus, the pollutant emission can be minimized and the combustion process matched to the optimal supply range of the respective engine.

Additionally or alternatively, the measuring device can also be used for an analysis of the exhaust of the combustion apparatus. The analytical result can be that a certain fraction of a known type of gas component of a gas mixture exceeds a limit value.

Also, control in the field of medicinal applications provides another opportunity. Thus, the above-described measuring device can be applied according to the invention for metering anesthetic gas.

The measuring device can be utilized for adjusting the ratio of individual components in the case of providing diving gas.

The measuring device can also be applied in a biogas reactor, especially utilized for exhaust gas measurement, polluting gas monitoring and/or composition monitoring of supplied and discharged gases.

Gas chromatographs are per se known. In many models, capillary like GC columns are arranged in a measuring chamber. If there are leakages, e.g. at the connection locations of the GC columns, then a measuring device arranged in the measuring chamber can detect these.

A measuring device arranged at the column end, respectively after the GC column, can additionally undertake the monitoring of the ratio of carrier gas to analyte. Thus, it is assured that the GC column is not overloaded by analyte, so that the chromatographic separation occurs optimally.

The measuring device can also by ascertaining the thermal properties, the viscosity and/or density of the measured medium perform a detection of a dangerous substance in an atmosphere, especially in air, and, in given cases, bring about a warning report, wherein the warning signal is matched to the type of the gases. In the case of an acoustic warning report, the sound sequence can e.g. indicate whether it concerns an explosive or poisonous, dangerous substance.

Also, the degree of purity of a one component gas or a gas mixture with a defined ratio of components can be monitored by means of the measuring device. A typical case of application would be e.g. checking the purity of sulfur hexafluoride $SF_6$.

The measuring device can be embodied as a handheld device. Thus, it can e.g. also be utilized for quality control at transfer points of pure- and very pure gases and, in given cases, output a warning report in the case of insufficient purity.

A further case of application for the measuring device of the invention relates to controlling the fuel supply in a fuel cell.

A special advantage of the measuring device and an application lies in the fact that the determining of a first thermophysical property and/or the determining of the viscosity $\mu$ and/or density $\rho$ of the measured medium (M) can be done by the measuring device in real time.

The terminology, real time, means in this connection time between the registering of a measured value and the output of an output value regarding a flow, one or more thermophysical properties, the viscosity, the density, the concentration, a mass fraction, a volume fraction and/or a partial pressure of at least one component or a plurality of components of a multicomponent, measured medium in a time span of less than three seconds, especially less than a second.

The measuring can thus especially also occur continuously and be output within the aforementioned maximum time period of less than three seconds e.g. to a user or a process control station.

The invention claimed is:

1. A measuring device, having:
at least a first component and additional components, wherein said at least a first component with said additional components form a measurement duct in the measuring device, wherein:
said measuring device is a thermal mass flow measuring device;
said measurement duct serves to conduct a measured medium;
said at least a first component is a multi-ply chip;
said at least a first component has a first sensor for determining at least one first thermophysical property selected from one of:
thermal conductivity, thermal diffusivity and/or specific heat capacity of the measured medium;
said first sensor is heatable and measures a temperature of the medium,
said first sensor is additionally provided for determining mass flow of the measured medium through said measurement duct;
said at least a first component further has a second sensor, which vibrates and is provided for determining viscosity and/or density of the measured medium;
said second sensor includes one or more cantilevers;
said first sensor and said second sensor are arranged inside the measuring duct;
the measured medium is conducted through said measuring duct from said first sensor to said second sensor;
said first sensor and second sensor are arranged on said at least a first component;
the determination of said at least one first thermophysical property occurs according to one of: the 3-omega method and the evaluating amplitude and phase of temperature measurement points of a temperature signal;
the measuring device has at least one evaluation unit, which determines from measured values measured by said first sensor and/or second sensor at least thermal conductivity $\kappa$, thermal diffusivity $\alpha$, specific heat capacity $\rho c_p$, viscosity $\mu$ and/or density $\rho$ of the measured medium; and
the evaluation unit ascertains concentration, volume fraction, mass fraction and/or partial pressure of said at least a first component in the measured medium, based on:
the measured values or at least two of the fluid properties ascertained from the measured values, and data sets relative to the fluid properties, and/or
values capable of being derived from the fluid properties for individual components and/or component mixtures, and corresponding with the fluid properties determined by the first sensor and the second sensor.

2. The measuring device as claimed in claim 1, wherein:
said first sensor has at least two passive sensor elements and a heater.

3. The measuring device as claimed in claim 2, wherein:
said heater includes at least one temperature sensor element and at least one heating element.

4. The measuring device as claimed in claim 2, wherein:
said at least two passive sensor elements are arranged asymmetrically to said heater.

5. The measuring device as claimed in claim 2, wherein:
said heater is excited periodically.

6. The measuring device as claimed in claim 1, wherein:
said cantilever is excited electromagnetically to execute oscillations.

7. The measuring device as claimed in claim 1, wherein:
said cantilever is affixed only unilaterally, while a second end is arranged to oscillate freely.

8. The measuring device as claimed in claim 1, wherein:
the measuring device is embodied as a handheld device with a connection to a valve.

9. The measuring device as claimed in claim 1, wherein the measuring device is applied for determining product characteristics of gases or liquids and/or the composition of a gas- or liquid mixture.

10. The measuring device as claimed in claim 1, wherein the measuring device is applied for determining concentration of at least one component of a gas mixture having known ingredients.

11. The measuring device as claimed in claim 10, wherein:
the gas mixture is a binary and/or ternary gas mixture.

12. The measuring device as claimed in claim 10, wherein:
the one component is an aliphatic hydrocarbon having a chain length of less than 4 C-atoms.

13. The measuring device as claimed in claim 10, wherein:
the concentrations of all components of the ternary gas mixture are determined.

14. The measuring device as claimed in claim 1, wherein the measuring device is applied determining methane fraction in a methane containing gas mixture.

15. The measuring device as claimed in claim 1, wherein the measuring device is applied for determining heating value of a combustible gas mixture.

16. The measuring device as claimed in claim 1, wherein the measuring device is applied for controlling flow of a measured medium, and wherein a control apparatus is operated as a function of the one first thermophysical property and the density of the measured medium.

17. The measuring device as claimed in claim 16, wherein:
the control apparatus is a mass flow controller.

18. The measuring device as claimed in claim 16, wherein:
the control of the flow of the medium includes control of the inflow and outflow of gases in a burning process of a combustion apparatus.

19. The measuring device as claimed in claim 18, wherein:
the measuring device is arranged in the combustion apparatus in the form of a combustion engine and the measuring device is applied for optimizing the combustion process in the combustion engine.

20. The measuring device as claimed in claim 16, wherein:
the measuring device is applied for analysis of the exhaust of the combustion apparatus.

21. The measuring device as claimed in claim 16, wherein:
the measuring device is applied for metering anesthetic gas in medicinal applications.

22. The measuring device as claimed in claim 16, wherein:
the measuring device is applied for setting a predetermined ratio of nitrogen to oxygen in the case of the providing of diving gas.

23. The measuring device as claimed in claim 1, wherein:
the measuring device is applied for exhaust gas measurement, polluting gas monitoring and/or composition monitoring of supplied and discharged gases in a biogas reactor.

24. The measuring device as claimed in claim 1, wherein the measuring device is included in a gas chromatograph for detecting leakages of carrier gas and/or for monitoring the ratio between carrier gas and analyte.

25. The measuring device as claimed in claim 1, wherein the measuring device is applied for detecting a dangerous substance in an atmosphere.

26. The measuring device as claimed in claim 1, wherein the measuring device is applied for monitoring degree of purity of one component gas or a gas mixture having a defined ratio of components.

27. The measuring device as claimed in claim 1, wherein the measuring device is applied for controlling fuel supply in a fuel cell.

28. The measuring device as claimed in claim 5, wherein:
the determining of a first thermophysical property and/or the determining of viscosity and/or density of the measured medium by the measuring device occurs in real time.

\* \* \* \* \*